United States Patent [19]

Louge

[11] Patent Number: 5,459,406
[45] Date of Patent: Oct. 17, 1995

[54] GUARDED CAPACITANCE PROBES FOR MEASURING PARTICLE CONCENTRATION AND FLOW

[75] Inventor: Michel Y. Louge, Ithaca, N.Y.

[73] Assignee: Cornell Research Foundation, Inc., Ithaca, N.Y.

[21] Appl. No.: 266,331

[22] Filed: Jul. 1, 1994

[51] Int. Cl.$^6$ .................................................. G01R 27/26
[52] U.S. Cl. ........................ 324/688; 324/690; 361/281
[58] Field of Search ........................................ 324/687, 688, 324/690, 347; 361/272, 278, 280, 281

[56] References Cited

U.S. PATENT DOCUMENTS

| | | | |
|---|---|---|---|
| 2,369,177 | 2/1945 | Raskhodoff | 361/278 |
| 2,389,241 | 11/1945 | Silverman | 324/347 |
| 2,800,628 | 7/1957 | Stinson et al. | 324/690 |
| 3,324,388 | 6/1967 | Davison | 324/688 |
| 3,388,325 | 6/1968 | Birdwell et al. | 324/347 |
| 3,635,082 | 1/1972 | Prellwitz et al. | |
| 3,678,378 | 7/1972 | Trott et al. | 361/278 |
| 3,729,994 | 5/1973 | Klub | |
| 3,781,672 | 12/1973 | Maltby et al. | |
| 3,811,087 | 5/1974 | Schmelzer | 324/688 |
| 3,879,644 | 4/1975 | Maltby | |
| 4,179,627 | 12/1979 | Reitz | 361/281 |
| 4,354,219 | 10/1982 | Akita | |
| 4,459,858 | 7/1984 | Marsh | |
| 4,468,609 | 8/1984 | Schmitz | 324/690 |
| 4,503,424 | 3/1985 | Evenwoll | |
| 4,509,366 | 4/1985 | Matsushita et al. | |
| 4,560,923 | 12/1985 | Hanson | 324/687 |
| 4,568,873 | 2/1986 | Oyanagi et al. | |
| 4,604,904 | 8/1986 | Massen | |
| 4,708,021 | 11/1987 | Braun et al. | |
| 4,817,021 | 3/1989 | Sowerby et al. | 324/687 |
| 4,845,421 | 7/1989 | Howarth et al. | |
| 4,920,795 | 5/1990 | Codazzi et al. | |
| 4,972,154 | 11/1990 | Bechtel et al. | |
| 5,017,879 | 5/1991 | Lucas et al. | |
| 5,081,421 | 1/1992 | Miller et al. | |
| 5,170,670 | 12/1992 | Fasching et al. | |
| 5,223,796 | 6/1993 | Waldman et al. | |
| 5,258,719 | 11/1993 | Miura et al. | |
| 5,270,664 | 12/1993 | McMurtry et al. | |

FOREIGN PATENT DOCUMENTS

| | | | |
|---|---|---|---|
| 0010754 | 1/1986 | Japan | 324/689 |
| 0642639 | 1/1979 | U.S.S.R. | 324/689 |

OTHER PUBLICATIONS

Lischer, D. Jeffrey et al., "Optical fiber measurements of particle concentration in dense suspensions: calibration and simulation", Applied Optics, vol. 31, No. 24, pp. 5106–5113, Aug. 20, 1992.

Louge, M. et al., "Measurements of the Effective Dielectric Permittivity of Suspensions", Powder Technology, 62, pp. 85–94, 1990.

(List continued on next page.)

Primary Examiner—Maura K. Regan
Attorney, Agent, or Firm—Jones, Tullar & Cooper

[57] ABSTRACT

Guarded capacitance probe structures are constructed with guard electrodes surrounding one or more sensor electrodes and ground electrodes or grounded surfaces surrounding the guard electrodes. In a one sensor embodiment, the probe utilizes an apertured sensor electrode and the guard electrode both surrounds the sensor electrode and fills the aperture. This embodiment is particularly useful for measuring particle concentration in a fluid suspension contained within a vessel or pipe. The portion of the guard electrode within the aperture of the sensor electrode prevents electric field lines from emanating from the sensor electrode into the fluid suspension and toward infinity. A two sensor embodiment of the probe is useful for measuring flow velocities of fluid suspensions through cross correlation of the outputs generated by each sensor. The relative dimensions of the guard and sensor electrodes are selected to provide the most accurate measurements by confining the electric lines emanating from the sensor electrode or electrodes and terminating on the surrounding grounded surfaces to a small measurement volume of the fluid suspension near the vessel or pipe wall.

7 Claims, 8 Drawing Sheets

OTHER PUBLICATIONS

Louge, M. et al., "Measurements of Voidage Near the Wall of a Circulating Bed Riser", Powder Technology, 62, pp. 269–276, 1990.

Riley; Catherine Acree et al., "Quantitative Capacitive Measurements of Voidage in Gas–Solid Flows," Particulate Science and Technology, 7:51–59, 1989.

GUARDED CAPACITANCE PROBES FOR MEASURING PARTICLE CONCENTRATION AND FLOW

This invention was made with Government support under Contract No. DE-AC22-91PC-90183, awarded by the Department of Energy. The Government has certain rights in the invention.

BACKGROUND OF THE INVENTION

The present invention relates in general to guarded capacitance probe structures that are particularly useful for non-invasively measuring particle concentration and/or particle flow.

Capacitance probes have been used in the past to measure particle concentration or flows non-invasively. These probes are based on the principle that the capacitance between two conductive surfaces (e.g. electrodes) held at different voltages can be varied by changing the nature of a dielectric substance placed within the electric field generated between them. Since the dielectric constant of a particle containing liquid or gas varies depending upon the particle concentration, a capacitance probe can be employed to measure particle concentration non-invasively by positioning it on a vessel or pipe containing the liquid or gas to be analyzed, and causing the electric field generated between the probe's electrodes to pass through a portion of the liquid or gas near the vessel or pipe wall. As the particle concentration in the liquid or gas varies, so does it dielectric constant, and thus, the capacitance of the probe also varies. If two of the capacitance probes are placed a predetermined distance from one another on the vessel or pipe, their outputs can also be employed to determine the flow rate of the liquid or gas through the vessel by cross correlating the signals generated by each probe to determine the difference in time when portions of the flow stream having like dielectric constant pass each of the probes, and dividing the distance between the probes by this time difference.

Traditional capacitance probes have suffered from the possible interference of other charged surfaces in their vicinity and from considerable reductions in the signal-to-noise ratio. associated with the capacitance of a cable connecting the output of the probe to a necessary signal amplifier. In order to solve these problems, numerous probes have been devised that include a guard electrode in addition to the sensor and ground electrodes found in traditional probes. One such prior art probe is illustrated in FIG. 1. In particular, a probe 10 is shown that is positioned contiguous to the outside surface of a pipe 12 containing a fluid suspension 14 to be monitored. The probe 10 includes a centrally disposed ground electrode 16, a coaxial sensor electrode 18 and a guard electrode 20. The sensor electrode 18 is connected to a source of voltage (not shown) by means of a coaxial conductor 22 and generates a plurality of curved electric field lines 24 which pass through a portion of the fluid suspension 14 near the wall of the pipe 12 and terminate on the ground electrode 16.

As is typical, the guard electrode 20 surrounds the sensor electrode 18 everywhere except where the measurement is to be made. The guard electrode 20 is driven by a separate circuit, but its voltage is precisely matched to that of the sensor electrode 18. Consequently, no charge can accumulate in the cable between the guard and the sensor so that cable capacitance is effectively cancelled. The guard electrode 20 also shields the sensor electrode 18 from any charged surface in the vicinity of the probe 10 so that stray capacitances are also virtually eliminated.

Unfortunately, prior art guarded capacitance probes suffer from one significant drawback. In particular, a large portion of the vessel or pipe wall must also be held at the guard voltage in order for this geometry to work in a non-invasive wall probe. This constraint constitutes a significant impediment to industrial measurements.

SUMMARY OF THE INVENTION

The present invention seeks to overcome the aforementioned drawback of previous guarded capacitance probe designs by providing guarded capacitance probes in which the relative locations of the three probe electrodes, i.e., sensor, ground and guard, are reversed. In a first embodiment, the probe's sensor electrode is formed in the shape of an axisymmetric ring and the guard electrode includes both a portion disposed within the middle of the ring, and an outer portion surrounding the ring. The ground electrode then lies outside the guard electrode and is created simply by grounding the wall of the vessel to which the probe is attached. The ring shaped sensor electrode is employed to insure that the electric field lines that it sheds toward ground are confined to the near vicinity of the probe so that a finite volume of the flow stream near the vessel wall will be covered by the electric field lines. If the sensor electrode were a solid circle, the field lines emanating from the center of the circle would continue straight through the vessel wall into the flow stream and toward infinity, thereby causing an inaccurate measurement.

The relative dimensions of the sensor and guard electrodes must therefore be chosen carefully to satisfy certain criteria. In particular, the sensor electrode must be close enough to the periphery of the probe so that the electric field lines that it sheds toward the ground are confined to the near vicinity of the probe. On the other hand, the sensor electrode must not be so close to the ground that the capacitance between these two surfaces becomes too large to detect. Mathematical calculations have been made to determine the range of relative dimensions of the sensor and guard electrodes which result in a probe of superior measurement accuracy.

The basic concept of the present invention can be embodied in capacitance probes of different configurations. In another embodiment, the sensor and guard electrodes are formed integrally along the inside wall of a conductive cylindrical pipe with the pipe again forming the surrounding ground electrode. In a third embodiment, two sensor electrodes are provided which are each surrounded by their own guard electrodes that are adjacent to one another. This configuration is particularly useful for measuring flow rates through cross correlation of the output signals from the two probes. In a variation of the two probe embodiment useful for flow measurement, the sensor and guard electrodes are formed as adjacent cylindrical rings disposed on a cylindrical rod which is inserted in a flow stream parallel to the direction of flow. In all of these alternative embodiments, the relative dimensions of the guard and sensor electrodes are chosen in the same manner as in the first embodiment so that the electric field lines formed between the sensor and ground electrodes are confined, while at the same time, the effect of variations in the probe dimensions on the capacitance and the extent of the measurement volume are minimized.

BRIEF DESCRIPTION OF THE DRAWINGS

The advantages and features of the present invention will become apparent from the following detailed description of a number of preferred embodiments thereof, taken in conjunction with the accompanying drawings, in which.

DETAILED DESCRIPTION OF THE PREFERRED EMBODIMENT

Figure 1:
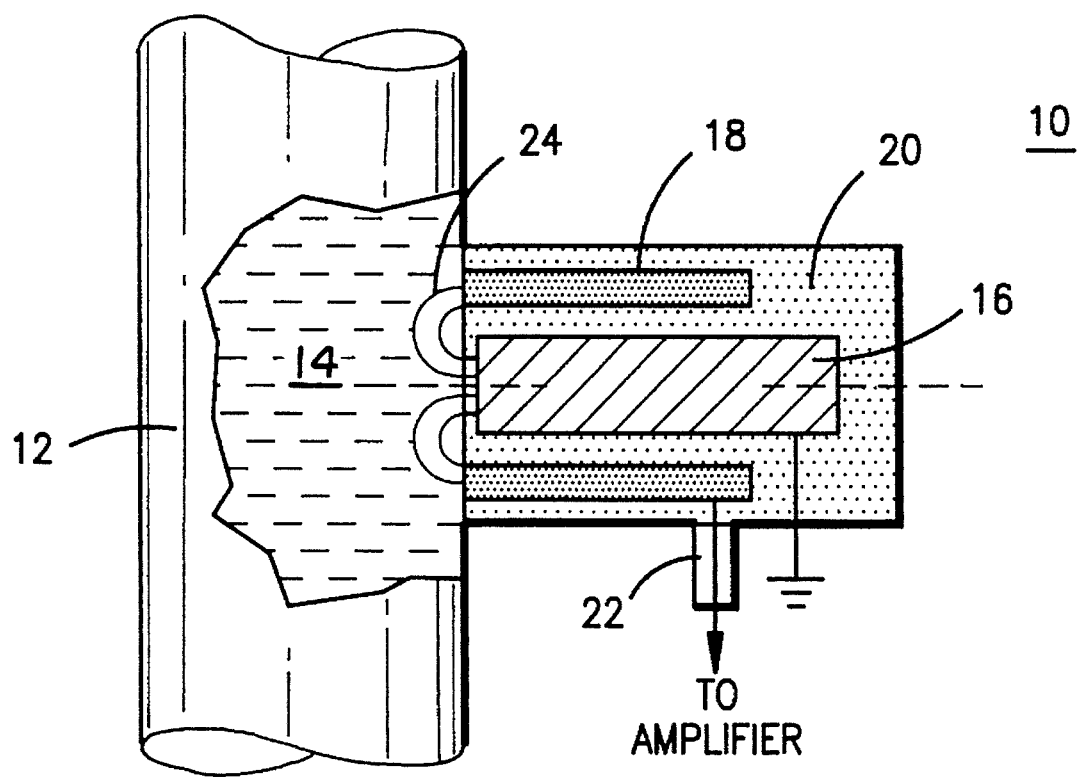
FIG. 1 is a schematic illustration of a prior art guarded capacitance probe.
Figure 2:
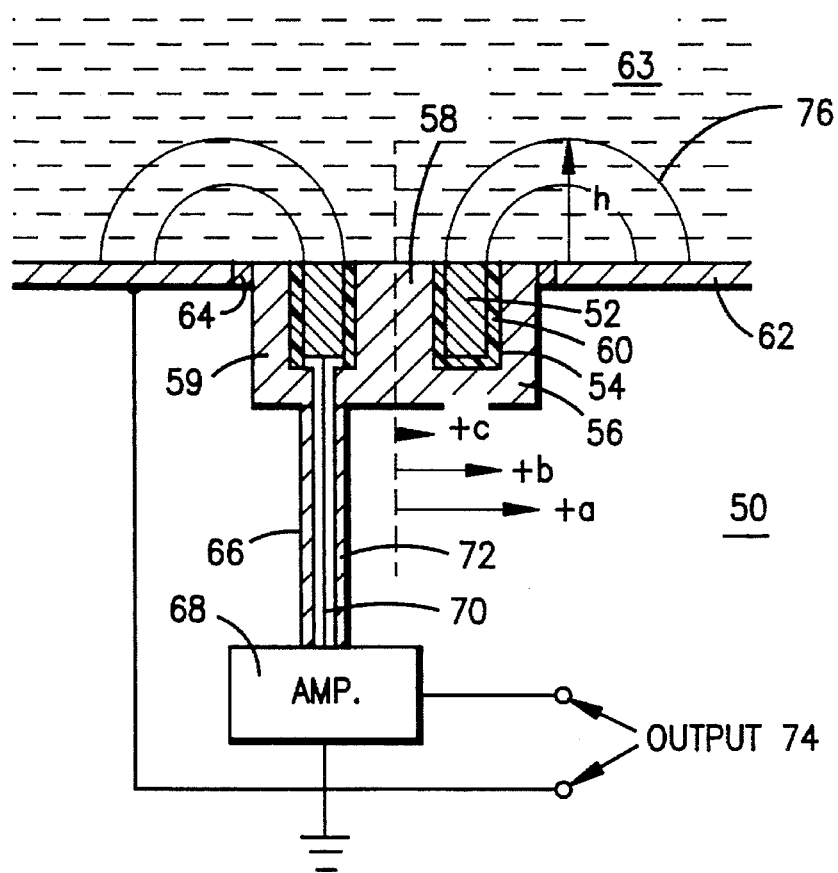
FIG. 2 is a schematic cutaway illustration of a guarded capacitance probe constructed in accordance with a first preferred embodiment of the present invention.
Figure 3:
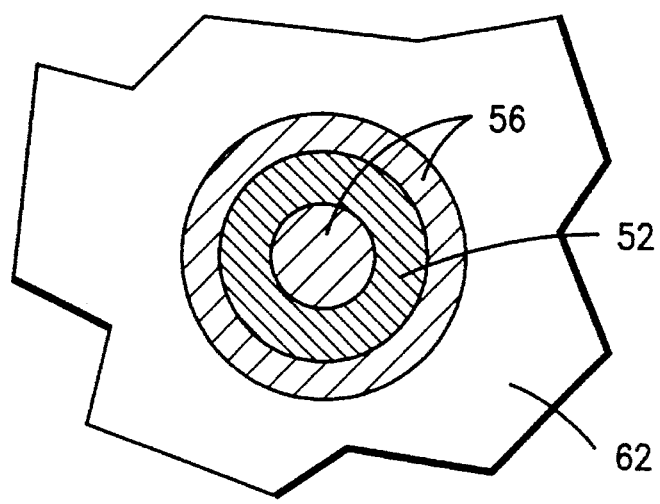
FIG. 3 is a schematic illustration of the front of the capacitance probe of FIG. 2.

Turning now to a more detailed consideration of a number of preferred embodiments of the present invention, FIGS. 2 and 3 illustrate a first preferred embodiment comprising a guarded capacitance probe 50. The probe 50 includes an apertured annular sensor electrode 52 which is received in a circular slot 54 formed in a cylindrical guard electrode 56 that surrounds the sensor electrode 52 on three sides. A central raised inner portion 58 of the guard electrode 56 substantially fills the aperture in the sensor electrode 52, while an outer portion 59 surrounds the sensor electrode 52. A thin insulation layer 60 is disposed between the walls of the slot 54 and the sensor electrode 52 which electrically insulates the guard electrode 56 from the sensor electrode 52.

The probe 50 is disposed in an aperture formed in a conductive wall 62 of a vessel or pipe containing a fluid (i.e., liquid or gas) suspension 63 whose concentration is to be measured. Another thin insulation layer 64 electrically insulates the conductive wall 62 from the guard electrode 56. The conductive wall 60 is electrically grounded so that it acts as a ground electrode for the probe 50.

A shielded coaxial cable 66 electrically connects the sensor electrode 52 and the guard electrode 56 to a conventional guarded capacitance probe amplifier 68, which by way of example can be either a Model 4000 series amplifier manufactured by Capacitec, Inc. of Ayer, Mass. or an Accumeasure System 1000 manufactured by MTI, Inc. of Latham, N.Y. This amplifier supplies a sinusoidal current of constant amplitude at a typical frequency of 16 kHz to the sensor electrode 52 through a central conductor 70 of the coaxial cable 66, and supplies a voltage through an outer conductor 72 of the coaxial cable 66 to the guard electrode 56, this voltage being automatically controlled so that it is equal to the varying voltage on the sensor electrode 52. The amplifier 68 generates a rectified voltage on an output 74 which is directly related to the particle concentration in the fluid suspension contained within the vessel or pipe as illustrated by the function in the graph of FIG. 4.

The sensor electrode 52 generates a plurality of curved electric field lines 76 which terminate on the grounded conductive wall 62 in such a manner that they encompass a measurement volume within the vessel or pipe that is confined close to the inner surface of the wall 62. The purpose of the guard electrode 56 is to protect the electric field lines 76 originating from the sensor electrode 52 from outside electrical interferences and stray capacitance. The central raised inner portion 58 of the guard electrode 56 also insures that no electric field lines emanate from the center of the sensor electrode 52 because they would travel in a straight line toward infinity, thus producing an inaccurate measurement. The outer portion 59 of the guard electrode 56 is sized so that the electric field lines emanating from the sensor electrode 52 will not immediately curve back upon themselves onto the grounded conductive wall 62 without passing through the fluid suspension, thus also causing an inaccurate measurement. The calculations employed for determining the optimum dimensions of the sensor electrode 52 and guard electrode 56 are discussed in detail below.

Figure 5:
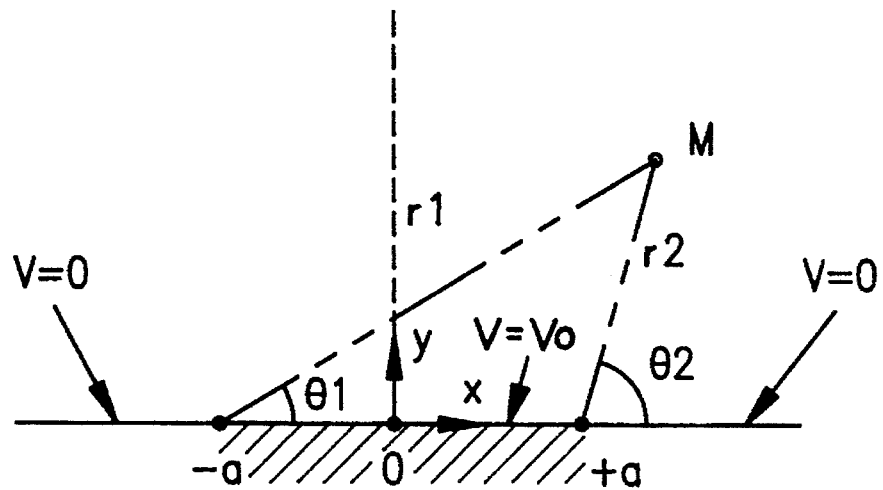
FIG. 5 is a graph of the complex plane of a two-dimensional system of electrical surfaces.

Before deriving the optimum dimensions of the grounded probe, it is useful to derive the pattern of electric field lines emanating from the two-dimensional system of electrical surfaces shown in FIG. 5. This geometry is convenient since the Laplace equation is identically solved upon finding analytical functions in the complex plane. Then it is straight-forward to extend the calculation to the axisymmetric geometry. This calculation is not original since it involves solving the Laplace equation in a classical geometry.

For convenience, consider a homogeneous medium above the planar electrodes of FIG. 5. The purpose is merely to find a complex function in the plane x,y that satisfies the following boundary conditions on the x-axis:

$V=V_o$ for $-a<x<+a$;

$V=0$ elsewhere.

The corresponding complex function is $$\Phi = \frac{V_0}{\pi}(-i\ln(z-a) + i\ln(z+a)), \quad (1)$$

where $i^2=-1$ and z is the location of point M in the complex plane. Defining $$z-a = r_1 \exp[i\theta_1] \quad (2a)$$

$$z+a = r_2 \exp[i\theta_2] \quad (2b)$$

then $$\Phi = \frac{V_0}{\pi}\left([\theta_1 - \theta_2] + i\ln\left(\frac{r_2}{r_1}\right)\right). \quad (3)$$

The corresponding lines of constant voltage V are such that the real part of $\Phi$ is constant and equal to V, $$V = (V_o/\pi)(\theta_1 - \theta_2) \quad (4)$$

The electric field lines form an orthogonal set.

On any field line the imaginary part of $\Phi$ is constant. Consequently, for a given field line, $$r_2/r_2 = \text{constant}. \tag{5}$$

The field lines are therefore a family of circles with center located on the axis. From (5) it can be shown that the field line centered at $x=x_c$ has a radius $R_c$ given by $$R_c/a = \sqrt{(x_c/a)^2 - 1}. \tag{6}$$

Note that because the field line is centered on the x-axis, its height above the plane is $R_c$. The guarded capacitance probe 50 can be described using this formalism.

Because the guard electrode 56 is maintained at the same voltage as the sensor electrode 52, the guard/sensor boundary is transparent to the pattern of electric field lines. In a homogeneous medium, the measurement volume is bounded by the electric field lines 76 emanating from the edges of the sensor electrode 52. A measure of its extent away from the plane is the height h of the outermost field line, $$h = (a^2 - c^2)/2c \tag{7}$$

This calculation also leads to a prediction of the capacitance of the corresponding axisymmetric arrangement. The electric field consistent with the complex potential $\Phi$ is $$E = -\text{grad } V; \tag{8}$$

The magnitude of E at the wall determines the charge distribution there, $$E = (\sigma/K\epsilon_o)n, \tag{9}$$

where $\epsilon_o = 8.854 \cdot 10^{-12}$ F/m is the dielectric permittivity of free space, K is the effective dielectric constant of the medium above the probe (K=1 for air; K≠1 for dielectrics), $\sigma$ is the charge density (C/m$^2$) and n is the outward normal to the plane. Combining (4), (8) and (9) yields $$\sigma = \frac{V_0 K \epsilon_0}{\pi} \left( \frac{1}{x+a} - \frac{1}{x-a} \right) \text{for } -a < x < +a. \tag{10}$$

The corresponding total charge Q on the sensor electrode of an axisymmetric probe is (FIG. 3)

$$Q = \int_{x=c}^{b} \sigma \, 2\pi x \, dx = 2a \, K\epsilon_0 \, V_0 \ln \left( \frac{a^2 - c^2}{a^2 - b^2} \right); \tag{11}$$

The resulting capacitance between ground and sensor electrodes of the axisymmetric embodiment of FIG. 3 is $$C = Q/V_0 = 2a \, K\epsilon_0 \ln \left( \frac{a^2 - c^2}{a^2 - b^2} \right). \tag{12}$$

Figure 4:
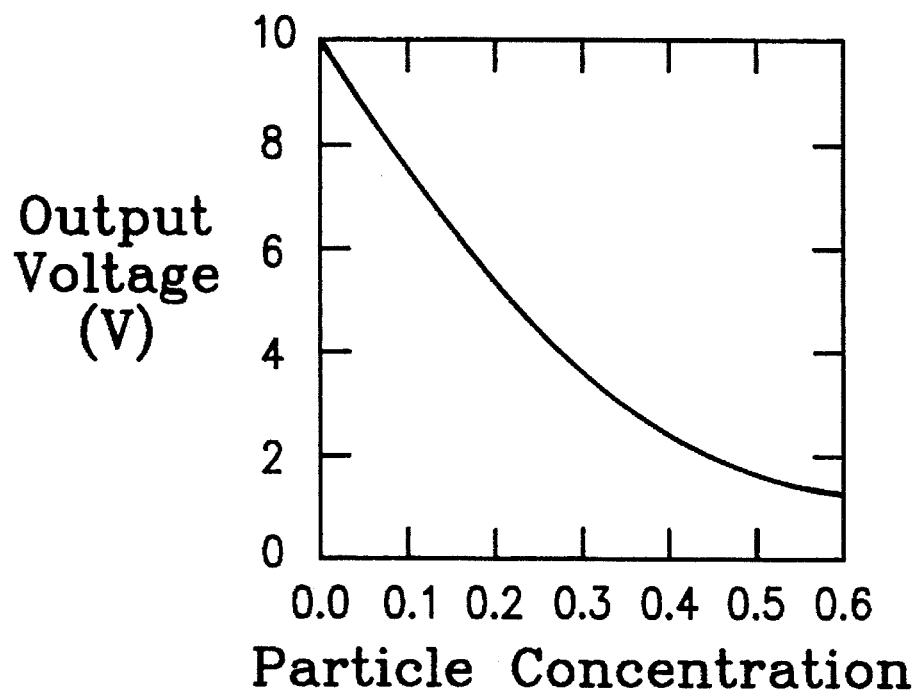
FIG. 4 is a graph illustrating the output voltage of the amplifier connected to the probe of FIG. 2 as a function of particle concentration in a dry fluid-cracking-catalyst.

In the amplifiers manufactured by MTI or Capacitec, the guard electrode voltage is rectified in a manner similar to that of an AM radio. The resulting dc voltage constitutes the amplifier's output V. This output is then proportional to the amplitude of the sensor electrode voltage. Because the sensor electrode is supplied by a current of constant amplitude, $$v = zi, \tag{13}$$

the amplifier output becomes proportional to the impedance Z between the sensor electrode and ground. In the case where the impedance is purely capacitive, $$z = 1/Cp, \tag{14}$$

where $p = i2\pi f$ and f is the frequency of the amplifier. Therefore, the amplifier output is inversely proportional to the capacitance between sensor and ground. In this case, one can measure the effective dielectric constant of the medium above the probe by recording the voltage output of the amplifier in the presence of air ($V_o$) and in the presence of the dielectric medium of interest (V). For media with a negligible imaginary part of K, $$K = C/C_o = V_o/V, \tag{15}$$

where $C_o$ is the capacitance of the probe in air. The voltage output for a typical industrial powder is shown in FIG. 4. For media with a significant imaginary part of K, the phase lag between V and i may be measured to infer the phase of K, while $V_o/V$ provides the magnitude of K.

Because it relies on a relative measurement, the dielectric constant can be determined with excellent accuracy. In the case of a suspension of solids, it remains to infer the concentration of the solids from the dielectric constant. A significant advantage of these types of capacitance probes is that they do not require any in situ calibration i.e., a calibration in the actual unit where the measurement is performed. Instead, it is sufficient to determine separately the effective dielectric properties of the suspension of interest. For suspensions with a well-known dielectric behavior this determination is even superfluous. For example, dielectric spheres satisfy the Meredith & Tobias model:

$$\frac{K}{K_h} = \frac{X - 2\phi + Y - 2.133 Z}{X + \phi + Y - 0.906 Z}, \tag{16}$$

where $X = (2K_h + K_p)/(K_h - K_p)$, $Y = 0.409\Phi^{7/3}(6K_h + 3K_p)/(4K_h + 3K_p)$, $Z = \Phi^{10/3}(3K_h - 3K_p)/(4K_h + 3K_p)$. In this expression, $\Phi$ is the particle volume fraction ("concentration"), and $K_p$ and $K_h$ are the dielectric constants of the material of the particles and the host medium respectively.

However, industrial powders are sometimes too complex to permit a straightforward model of their effective properties. In some cases, it is therefore necessary to establish the dependence of K on particle concentration through independent calibration experiments.

Because the pattern of electric field lines that emanates from the guard/sensor electrodes is not bounded, the challenge with a grounded capacitance probe is to confine the measurement volume near the probe. In the axisymmetric embodiment of FIG. 3 for example, the field line originating from the centerline of the probe is a straight line perpendicular to the plane. Therefore it is essential to avoid placing the electrode's surface at the center of the probe. Failing to do this would make it very difficult to interpret the signal, as the far away structure of the suspension would influence the character of the signal.

To confine the measurement volume it is natural to bring the sensor electrode's surface closer to the singularity at x=a. As Eq. (7) indicates, increasing the value of c reduces h. However, increasing c makes it more difficult to control the value of the probe's capacitance. In the extreme where b and c nearly equal a, the value of the capacitance is very difficult to predict, as it becomes excessively sensitive to small excursions in the values of c/a and b/a. The simple sensitivity analysis that follows captures this effect.

Rewrite Eq. (12) in dimensionless form, $$C^\dagger \equiv \frac{C}{2aK\epsilon_0} = \ln\left(\frac{1-c^{\dagger 2}}{1-b^{\dagger 2}}\right), \quad (17)$$

where $b^\dagger \equiv b/a$ and $c^\dagger \equiv c/a$. Consider separately the effects of a small error in the ratios $b/a$ and $c/a$. These errors could result, for example, from machining tolerances or from the deterioration of the probe after prolonged use in an industrial facility. Differentiating (17) yields $$\frac{\partial C^\dagger}{C^\dagger} = +\frac{2b^\dagger}{(1-b^{\dagger 2})\ln\left[\frac{1-c^{\dagger 2}}{1-b^{\dagger 2}}\right]} \partial b^\dagger \quad (18a)$$

$$\frac{\partial C^\dagger}{C^\dagger} = -\frac{2c^\dagger}{(1-c^{\dagger 2})\ln\left[\frac{1-c^{\dagger 2}}{1-c^{\dagger 2}}\right]} \partial c^\dagger \quad (18b)$$

It is reasonable to assume that the errors in $b^\dagger$ and $c^\dagger$ are statistically uncorrelated and both equal to $t/a$, where $t$ is a characteristic uncertainty common to b and c, $$\Delta b^\dagger = \Delta c^\dagger = t/a. \quad (19)$$

The parameter t may be interpreted, for example, as a mechanical tolerance in the construction of the probe. In this case, the relative error in $C^\dagger$ may be written $$\frac{\Delta C^\dagger}{C^\dagger} = \quad (20)$$

$$\left(\frac{t}{a}\right) \left\{ \frac{2}{\ln\left[\frac{1-c^{\dagger 2}}{1-b^{\dagger 2}}\right]} \sqrt{\frac{b^{\dagger 2}}{(b^{\dagger 2}-1)^2} + \frac{c^{\dagger 2}}{(c^{\dagger 2}-1)^2}} \right\}$$

In order to limit $\Delta C^\dagger/C^\dagger$, one should minimize the term in curly brackets.

Similarly, it is judicious to minimize excursions in the height of the measurement volume that would result from uncertainties in $c/a$. Defining $h^\dagger \equiv h/a$, Eq. (7) may be differentiated to give:

$$\frac{\partial h^\dagger}{h^\dagger} = \left(\frac{1+c^{\dagger 2}}{c^\dagger - c^{\dagger 3}}\right)\partial c. \quad (21)$$

Assuming again that the uncertainty in $c/a$ is $\Delta c^\dagger = t/a$, (21) yields $$\Delta h^\dagger/h^\dagger = \left(\frac{1+c^{\dagger 2}}{c^\dagger - c^{\dagger 3}}\right)(t/a). \quad (22)$$

In order to limit the relative uncertainty in $h^\dagger$, one should minimize the term in parentheses. This is achieved with $$c^\dagger_{min} = \sqrt{\sqrt{5} - 2} \approx 0.4859. \quad (23)$$

Substituting this value of $c^\dagger$ in (20), the value of $b^\dagger$ that minimizes the term in curly brackets in that equation is $$b^\dagger_{min} \approx 0.8221. \quad (24)$$

Thus, for the axisymmetric embodiment of FIG. 3, the optimum relative dimensions of the probe are $b/a \approx 0.8221$ and $c/a \approx 0.4859$. These dimensions of the probe make its capacitance and the extent of its measurement volume least sensitive to machining tolerances or deterioration of its front surface in an industrial environment. Because unintentional excursions of the measurement volume are minimized, these dimensions permit robust measurements and unambiguous interpretation of the probe signals in terms of local concentration.

Other embodiments of the grounded capacitance probe need not be axisymmetric. However, they should exhibit the following general configuration:

- a guard electrode surface where straight field lines emerge from the plane;
- a sensor electrode surface surrounded by the guard electrode on all sides except at the probe face where the measurement is carried out;
- a connection to the amplifier through a shielded cable whose center and exterior conductors are held at the sensor and guard electrode voltages, respectively;
- a ground surface or electrode at the periphery of the probe.

Whatever the geometry, three criteria yield optimum probe dimensions:

- the sensor surface electrode should not exhibit straight field lines perpendicular to the probe face;
- the capacitance between sensor electrode and ground and the height of the measurement volume should be as insensitive as possible to small excursions in the probe dimensions.

Many industrial applications require capacitance probes to be mounted flush with the inside surface of a grounded pipe. Because in this case the grounded surface on the opposite wall facing the probe may attract electric field lines from the sensor electrode surface, the measurement volume may exhibit an excessive extent away from the probe. For a probe of fixed dimensions, the risk associated with this situation increases with decreasing pipe diameter. The purpose of the following calculation is to establish a criterion valid for cylindrical pipes in the presence of a probe embodiment consisting of long surfaces parallel to the axis of the pipe. This geometry is unlikely to be employed in a real industrial situation. However, because it permits analytical solutions for the electric field, it is employed to illustrate the present discussion.

Figure 6:
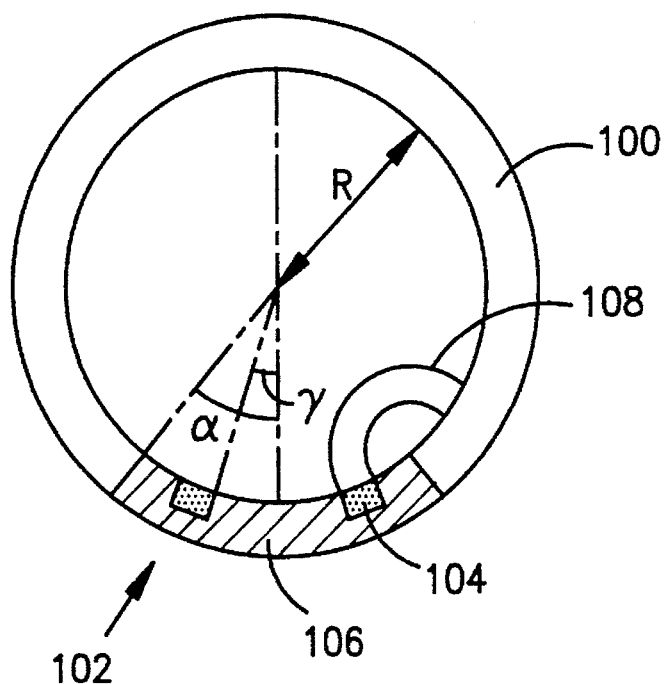
FIG. 6 is a schematic illustration of a second preferred embodiment of the present invention.
Figure 7:
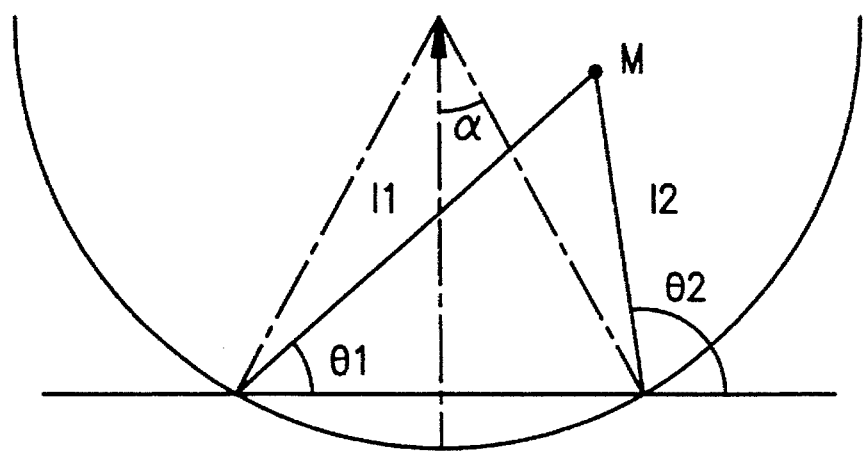
FIG. 7 is a graph illustrating the notation for the geometry of the second preferred embodiment.

Consider the cylindrical pipe 100 of FIG. 6 in which a guarded capacitance probe 102 is formed integrally in the wall of the pipe 100. Similar to the probe 50 of the FIG. 2 embodiment, the probe 102 includes an apertured sensor electrode 104 which is surrounded on three sides by a guard electrode 106. When power is supplied to the sensor electrode 104, an electric field is generated as indicated by the field lines 108 which penetrates a portion of the volume within the pipe 100 and terminates on the inner surface of the pipe 100 since it is grounded. As before, the height of the measurement volume is defined as the extent of the outermost field line above the pipe wall. In this configuration, the complex potential can be obtained by mapping the solution of (1) into a cylindrical geometry, $$\Phi = \frac{V_0}{\pi} i\,(\ln(r_2/r_1) + i\,(\theta_2 - \theta_1 + \alpha)), \quad (25)$$

where $\alpha$ is the angle shown in FIG. 6 and $r_1$, $r_2$, $\theta_1$ and $\theta_2$ are shown in FIG. 7. The corresponding height of the measurement volume is $$\frac{h}{R} = 1 + \frac{R_c}{R} - \sqrt{1 + \left(\frac{R_c}{R}\right)^2}, \tag{26}$$

where $$\frac{R_c}{R} = -\frac{\cos(\alpha)}{\sin(\gamma)} + \frac{1}{\tan(\gamma)}, \tag{27}$$

where $\gamma$ is shown in FIG. 6.

In order to confine the measurement volume near the wall of the pipe 100, h must be within a small fraction $\epsilon$ of the radius of the pipe, $$h/R < \epsilon << 1. \tag{28}$$

In this formulation, $\epsilon$ is the maximum relative extent of the measurement volume that the designer is willing to accept. The solution of (26) indicates that this condition is nearly equivalent to $$R_c/R < \epsilon, \tag{29}$$

or expanding (27) in series and retaining the lowest order terms, $$(\alpha^2 - \gamma^2)/2\gamma < \epsilon. \tag{30}$$

Note that the angles $\alpha$ and $\gamma$ are nearly equal to a/R and c/R, respectively. Therefore, (30) may be written as $$\frac{a}{R} \left( \frac{1 - c^{\dagger 2}}{2c^{\dagger 2}} \right) < \epsilon. \tag{31}$$

Using the optimum value of c† from (23), the following criterion is found:

$$a/R < 2\epsilon c_{min}^{\dagger}/(1 - c_{min}^{\dagger 2}). \tag{32}$$

or $$a/R < 1.27\epsilon. \tag{33}$$

An inspection of (32) shows that in the limit of small $\epsilon$ it is equivalent to (7). Therefore, if the measurement volume remains confined near the wall (h/R<<1), the cylindrical pipe behaves no differently than an infinite flat wall.

Figure 8:
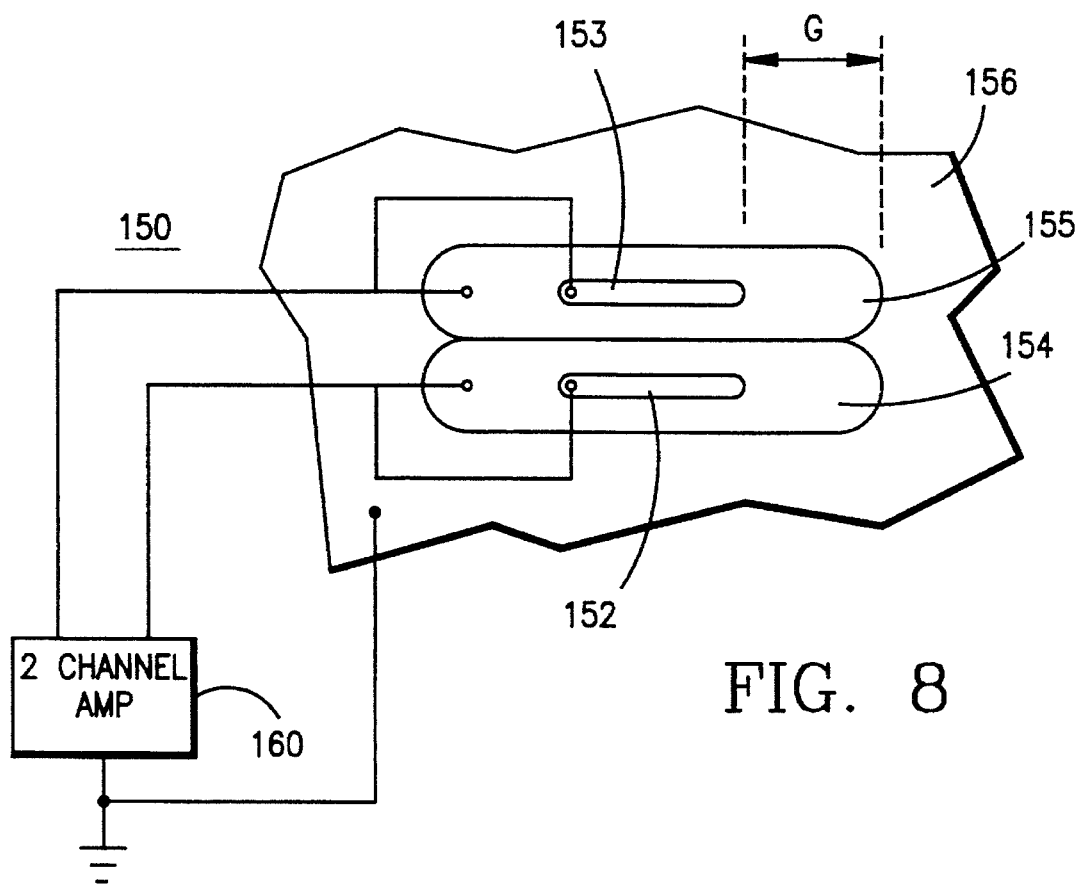
FIG. 8 is a schematic illustration of a third preferred embodiment of the present invention.

Another useful embodiment of the present invention is illustrated in FIG. 8. In particular, a two sensor guarded capacitance probe 150 is illustrated which includes first and second sensor electrodes 152 and 153, each of which is surrounded by its own guard electrode, 154 and 155, respectively. As illustrated, the two guard electrodes 154 and 155 are contiguous to one another along one of their edges, although they are electrically insulated from one another by a thin layer of insulation (not shown). As with the other capacitance probes, the surface surrounding the guard electrodes 154 and 155 is grounded and therefore acts as a ground electrode 156. The idea behind this two sensor embodiment is to drive the guard and sensor electrodes by two separate channels of an amplifier 160 having synchronous current sources of constant amplitude. One such amplifier is also manufactured by Capacitec, Inc. In addition to recording the local concentration as before, each sensor electrode 152 and 153 can now detect separately the passage of a disturbance in the local dielectric constant. If such a disturbance travels at a finite speed above the probe 150, the cross-correlation of the signals from the two amplifier channels can yield its time-of-flight, hence its velocity.

Figure 9:
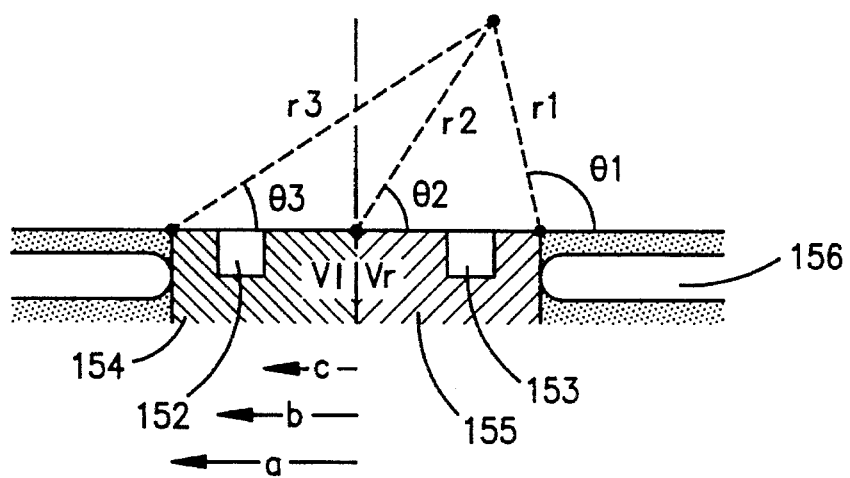
FIG. 9 is a graph illustrating the complex plane for the electrical surfaces of the probe of FIG. 8.

An approximate calculation needs to be carried out leading to the optimum dimensions of the probes that will avoid shedding straight electric field lines perpendicular to either of the two sensor electrode surfaces. To illustrate this new calculation, it is assumed that the probe face is narrow, so the pattern of electric field lines is nearly two-dimensional. In this case, because the two current sources are nearly in phase, the electrical surfaces of the probe 150 can be sketched as shown in FIG. 9.

Because in general the two sensor electrodes 152 and 153 (left and right, respectively, in FIG. 9) are exposed to different local concentrations in their vicinity, they experience a slightly different pattern of electric field lines and, consequently, they exhibit two different voltages $V_l$ and $V_r$. The ratio of these voltages is defined as $$\gamma = V_l/V_r, \tag{34}$$

Because in a flowing suspension inhomogeneities appear randomly in front of the two sensors, $\gamma$ is a function of time. However, because in typical suspensions the oscillating frequency of the amplifier is much larger than a characteristic time for the evolution of these inhomogeneities, a given value of $\gamma$ persists long enough to establish a steady pattern of electric field lines. In principle, this pattern depends on the detailed structure of the suspension since the dielectric permittivity $\epsilon = K\epsilon_o$ is a function of position. For simplicity, it is assumed in the present calculations that the suspension above the probe is homogeneous enough with the average dielectric permittivity $\bar{\epsilon}$ to establish the following complex potential:

$$\Phi = -\frac{i}{\pi} (V_r \ln[r_1 e^{i\theta_1}] + (V_l - V_r)\ln[r_2 e^{i\theta_2}] - V_l \ln[r_3 e^{i\theta_3}]). \tag{35}$$

The corresponding electric field lines are described by the equation $$\frac{r_1 \cdot r_2^{\gamma-1}}{r_3^{\gamma}} = \text{constant} \tag{36}$$

or in cartesian coordinates, $$\frac{[(x-a)^2 + y^2][x^2 + y^2]^{\gamma-1}}{[(x+a)^2 + y^2]^{\gamma}} = \kappa, \tag{37}$$

where $\kappa$ is a constant. This equation may be used to identify where straight field lines rise from the plane. For such lines the gradient of $\kappa$ is horizontal, $$\nabla \kappa \cdot y = 0, \tag{38}$$

or equivalently, from (37), $$\left(\frac{x}{a}\right)^3 + \frac{3}{2}\left(\frac{1-\gamma}{1+\gamma}\right)\left(\frac{x}{a}\right)^2 - \frac{1}{2}\left(\frac{1-\gamma}{1+\gamma}\right) = 0. \tag{39}$$

There is only one real solution to this equation. It is $$\frac{x_1}{a} = -\rho + \rho^2/D + D, \tag{40}$$

where $$\rho \equiv (1/2)(1-\gamma)/(1+\gamma)$$

-continued and $$D \equiv [(\rho/2) - \rho^3 + \sqrt{-\rho^6 + (\rho^3 - \rho/2)^2}\,]^{1/3}.$$

For the potential of (35) the charge density is $$-\frac{\pi\sigma}{\epsilon} = \frac{V_r}{x-a} + \frac{V_l - V_r}{x} - \frac{V_l}{x+a}, \quad (41)$$

where $\epsilon$ is the value of the dielectric permittivity at the location x. Combining equations (34) and (41) reveals that the local charge vanishes at the location $$\frac{x_2}{a} = -\frac{1-\gamma}{1+\gamma}. \quad (42)$$

Figure 10:
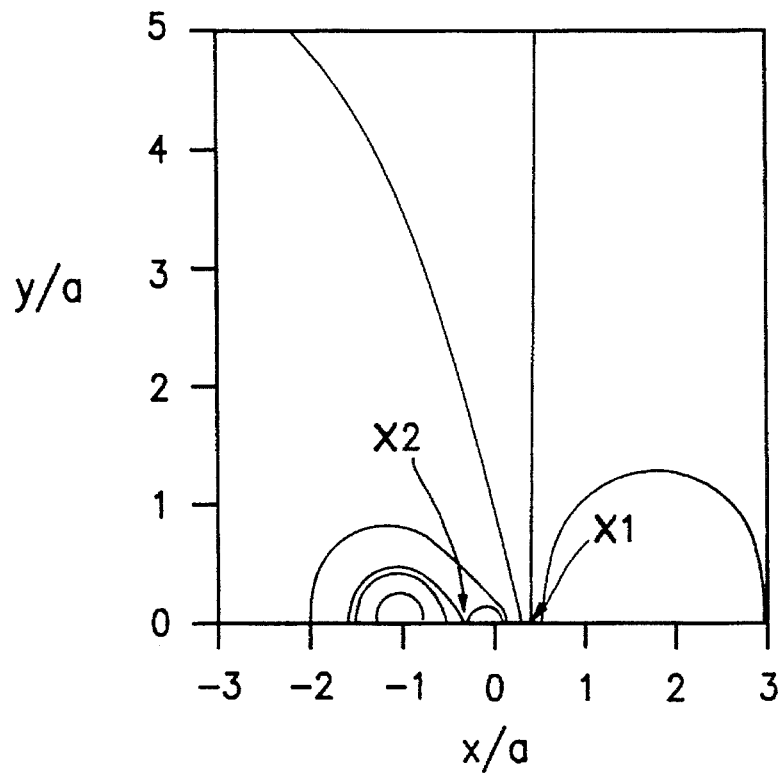
FIG. 10 is a graph illustrating the pattern of electric field lines generated by the probe of FIG. 8 for RMS voltage ratio $\gamma=0.5$.

A typical pattern of electric field lines is sketched in FIG. 10 for $\gamma=0.5$. In FIG. 10 the straight, vertical field line at the location $(x_1/a)$ defined by (40) is distinguished, and observe that electric field lines accumulate around the location $(x_2/a)$ where the local charge vanishes (Eq. 42). This pattern dictates the placement of the sensor surfaces outside the vertical field line, $$c/a < |x_1/a|, \quad (43)$$

where $x_1/a$ is given by (40) in terms of $\gamma$. Further, in order to ensure that the measurement volume always extends outward, it is also judicious to locate the sensor surfaces outside the point where the charge vanishes, $$c/a < |x_2/a|, \quad (44)$$

where $x_2$ is a function of $\gamma$ through (42). Note that this latter constraint is not as compelling as that of (43), since failure to enforce it would not lead to measurement volumes of excessive extent.

Upon integrating (41) over the area of the two sensor electrodes 152 and 153, the ratio of the total charges on these is $$\frac{q_l}{q_r} \approx \frac{\epsilon_l}{\epsilon_r}\left(\frac{\gamma-\lambda}{1-\gamma\lambda}\right), \quad (45)$$

where $q_l$ and $q_r$ are the charges on the left and right sensor electrodes 152 and 153 of FIG. 9, respectively, and the constant $\lambda$ combines physical dimensions of the probe 150, $$\lambda \equiv \ln\left[\left(\frac{a+c}{a+b}\right)\left(\frac{b}{c}\right)\right] / \ln\left[\left(\frac{a-c}{a-b}\right)\left(\frac{b}{c}\right)\right] = \quad (46)$$

$$\ln\left[\left(\frac{1+c\dagger}{1+b\dagger}\right)\left(\frac{b\dagger}{c\dagger}\right)\right] / \ln\left[\left(\frac{1-c\dagger}{1-b\dagger}\right)\left(\frac{b\dagger}{c\dagger}\right)\right],$$

where $0<\lambda<1$. Because the amplifier 160 supplies the two sensor electrodes 152 and 153 with an oscillating current of the same amplitude and nearly the same phase, the ratio of the total charges in (45) nearly equals one. Thus from (45), the ratio $\gamma$ satisfies $$\frac{\epsilon_r}{\epsilon_l} \approx \left(\frac{\gamma-\lambda}{1-\gamma\lambda}\right). \quad (47)$$

If the suspension is homogeneous, the permittivities $\epsilon_l$ and $\epsilon_r$ are equal and (47) yields $\gamma=1$. In this case, the probe 150 has an electric field pattern identical to that of the probe 50 of FIG. 2. In the suspension of greatest inhomogeneity, one of the sensor electrodes 152 or 153 is covered with a closely packed suspension of dielectric constant $K_{max}$ while the other is held in air. Because the probe 150 is symmetrical about its central axis, it may be assumed without loss of generality that the greatest inhomogeneity occurs when the left sensor electrode 152 is covered, while the right sensor electrode 153 is clear. The pattern of FIG. 10 approximates this situation. In this case, $\epsilon_r/\epsilon_l=1/K_{max}$. Therefore, from the least to the most homogeneous suspension, $$(1/K_{max}) \leq \epsilon_r/\epsilon_l \leq 1. \quad (48)$$

Combining (47) and (48) provides a conservative lower bound for $\epsilon$, $$\frac{1+\lambda K_{max}}{\lambda + K_{max}} \leq \gamma \leq 1. \quad (49)$$

Unlike the conditions of (43) and (44), this lower bound combines all physical dimensions of the probe through $\lambda$ and it is specific of a given value of $K_{max}$.

The last constraint on the design of the two sensor probe is derived from the earlier analysis of the probe 50 with a single sensor electrode. When the suspension is homogeneous, $\gamma$ is unity and the two sensor probe has an identical pattern of field lines as the single sensor probe. In this case, for a given c†, it is judicious to choose the value of b† that minimizes the term in curly brackets of (20). This renders the excursions in the probe capacitance least sensitive to errors in b† or c†. To satisfy this condition, a least-squares fit shows that c† and b† should be related by the approximate expression $$b^\wedge \approx 0.35c\dagger + 0.65 \quad (50)$$

for design values of c† in the range $0.2 \leq c\dagger \leq 0.9$. Using (50) to eliminate b† in (46), the lower bound for $\gamma$ in (49) is found to be a function of c† and $K_{max}$ alone.

Therefore for a given value of $K_{max}$, the optimum dimensions of the probe 150 should satisfy the four constraints of Eqs. (43), (44), (49) and (50). To summarize, these conditions achieve the following objectives:

Equation (43)→prevent vertical field lines from originating on the sensor electrode surfaces;

Equation (44)→ensure that the measurement volume extends outward from the sensor electrode;

Equation (49)→recognize a conservative lower bound for $\gamma$;

Equation (50)→make the capacitance least sensitive to errors in physical dimensions.

Figure 11:
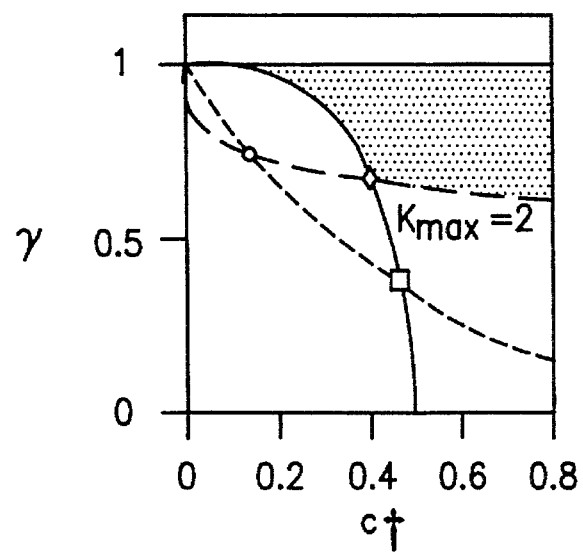
FIG. 11 is a graph illustrating limiting values of $X_1/a$, $X_2/a$ and $b/a$ represented as a function $\gamma$ vs. $c/a$ where the value of the dielectric constant, $K_{max}=2$.
Figure 12:
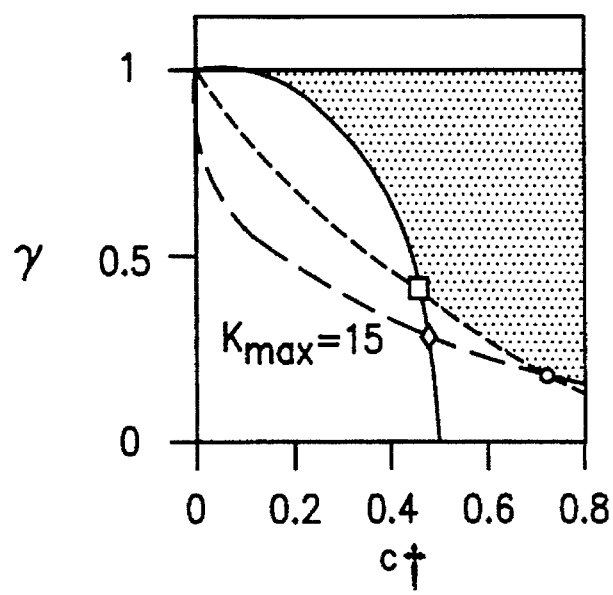
FIG. 12 is a graph illustrating the same functions as in FIG. 11 but with $K_{max}=15$.

It is convenient to plot these constraints on a single graph. In FIGS. 11 and 12, the region above the heavy solid lines represents values of $\gamma$ and c† where no vertical field lines originates from the sensor (Eq. 43). The region above the dotted line is where the sensor electrode does not include the point where the charge vanishes (Eq. 44). For given values of c†, possible values of $\gamma$ may be found in the region between the line $\gamma=1$ and the dashed line. In these figures, the shaded areas represent values of c† and $\gamma$ where all constraints are satisfied.

Two cases may now arise. The first concerns relatively low values of $K_{max}$ (FIG. 11). Here any value of $c\dagger$ to the right of the diamond may be chosen. For these values, by virtue of (49) and (50), the magnitude of $\gamma$ will always be such that the point $(c\dagger, \gamma)$ lies in the shaded area of the graph.

The second case is for large values of $K_{max}$ (FIG. 12). Here, in order to satisfy the constraint of (44) it is necessary to select a value of $c\dagger$ to the right of the open circle. For example, if values of $c\dagger$ between the diamond and the circle are chosen, possible values of $\gamma$ located in the dashed region of FIG. 12 would fail to satisfy (44).

Figure 13:
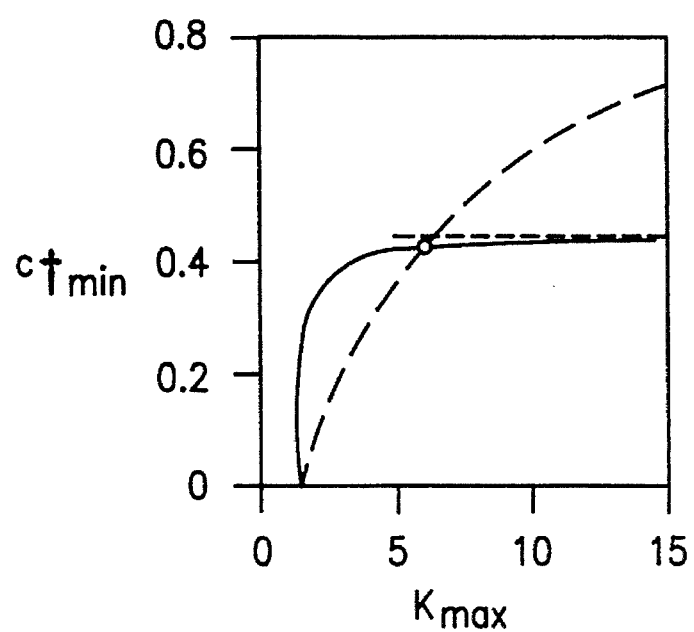
FIG. 13 is a graph illustrating the minimum design values of $c/a$ versus the maximum expected value of the suspension dielectric constant $K_{max}$; and, FIG. 14 is a schematic illustration of another two sensor capacitance probe constructed in accordance with the third preferred embodiment of the present invention.

In FIG. 13, the minimum design values of $c\dagger$ are plotted in terms of the maximum dielectric constant $K_{max}$ expected for a given suspension. For values of $c\dagger$ above the solid curve, no straight electric field line originates from any of the sensor electrodes. For values of $c\dagger$ above the dashed curve, the sensor electrodes do not exhibit a point where the charge vanishes. The two curves intersect at a critical value of the maximum dielectric constant $K_{max}^{crit} \approx 5.77$. Because the solid line of FIG. 13 asymptotes to $c\dagger \approx 0.4741$, all constraints are satisfied with $c\dagger \geq 0.4741$ provided that $K_{max} \leq 5.77$. In this case, the optimum value of $c\dagger = \sqrt{\sqrt{5}-2}$ used in the single sensor probe is recommended, since this value minimizes the error in $\Delta h\dagger/h\dagger$ as well.

In the case where $K_{max} > 5.77$, the most restrictive constraint is associated with the location of the vanishing charge point (Eq. 44). Unfortunately, if this constraint is satisfied, the resulting minimum value of $c\dagger$ grows with $K_{max}$. An empirical fit of the minimum value of $c\dagger$ is $$c\dagger_{min} \geq 1-\exp[-1.449 \; 10^{-5}(K_{max}-3)^3+1.806 \; 10^{-3}(K_{max}-1)^2-0.098(K_{max}-1)-0.212] \quad (51)$$

in the range $5.77 \leq K_{max} \leq 50$. As $c\dagger$ approaches unity, it becomes increasingly difficult to construct probes with such narrow sensor electrode surfaces. In this case, it is recommended that the constraint (51) be relaxed. The resulting consequences of a failure to enforce (44) are not very serious. In this case, the measurement volume delimited by the electric field lines emanating from one of the sensor electrodes may extend inward as well as outside the probe.

The last design issue of the two sensor probe concerns the lateral extent of the guard electrode surface. In order to protect the electric field lines of the sensor electrodes from the effects of the ground at either end of the probe, it is necessary to extend the guard electrode 154 over a sufficient distance G as illustrated in FIG. 8. A reasonable prescription of the minimum distance is $$G \leq P, \quad (52)$$

where P is the perimeter of the outermost electric field line emerging from the sensor electrode surface. For simplicity, this perimeter is calculated with $\gamma=1$. From (7), it is $$P=\pi h=\pi(a^2-c^2)/2c=\pi a(1-c\dagger^2)/2/c\dagger. \quad (53)$$

Thus, the following condition is imposed:

$$G/a \geq \pi a(1-c\dagger^2)/2c\dagger. \quad (54)$$

To summarize, the following design criteria are proposed:

for $K_{max} \leq 5.77 \rightarrow$ make $c\dagger=\sqrt{\sqrt{5}-2}$ and $b\dagger=0.8221$;

for $K_{max} > 5.77 \rightarrow$ make $c\dagger \leq c\dagger_{min}$ from (51) if construction permits; and make $b\dagger=0.35c\dagger+0.65$.

Figure 14:
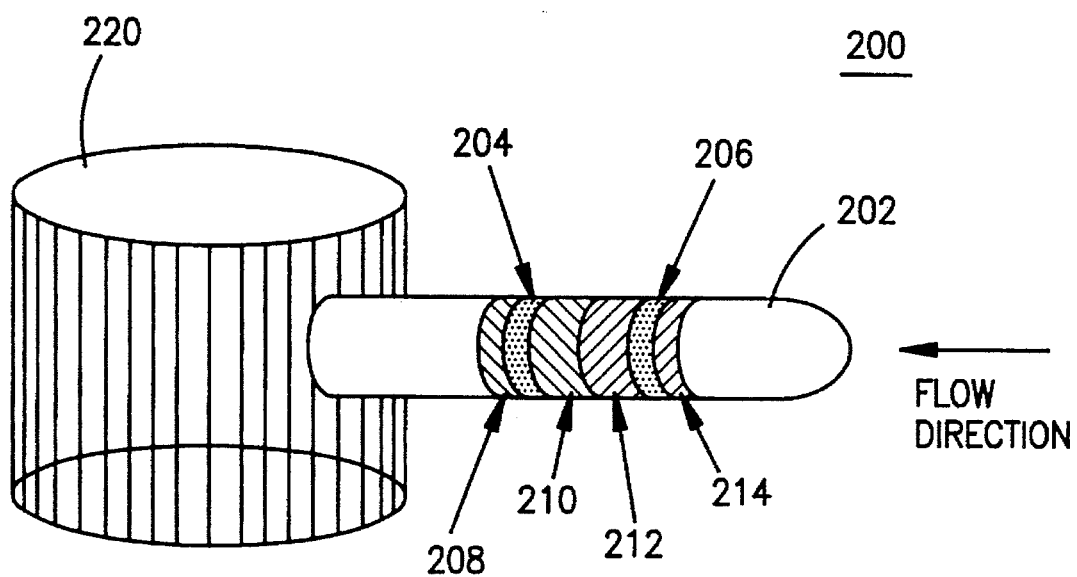

FIG. 14 illustrates another variation of the two sensor probe embodiment. In particular, a two sensor guarded capacitance probe 200 is shown in which a plurality of annular ring electrodes are mounted on a grounded cylindrical rod 202. The electrodes include first and second sensor electrodes 204 and 206 and four guard electrodes 208, 210, 212 and 214. All of the electrodes are electrically insulated both from one another and from the grounded conductive rod 202. The operation of the probe 200 is the same of that of the probe 150 of FIG. 8, and the relative dimensions of the various electrodes are calculated in the same manner as well.

The probe 200 of FIG. 14 is particularly useful for measuring material flows passed a pylon 220 on which the cylindrical rod 202 is mounted. A particular application of the two sensor probe 200 is in measuring variations in snow density and velocity in an avalanche flowing across the test pylon 220. This is a particularly useful application because the physics of snow avalanche flows are far from being well understood and economic and mortality costs due to avalanche hazards continue to escalate. If the probe 200 is positioned as illustrated so that the flow direction of the avalanche is parallel to the longitudinal axis of the rod 202, the probe 200 can be employed to measure simultaneously the density and velocity of the snow flowing passed the test pylon 220. Experiments have established that the magnitude of the effective dielectric constant for dry snow is a linear function of density and that the resulting $K_{eff}$ is large so that the signal-to-noise ratio in the flow will be very strong. The two sensor capacitance probe 200 can thus record accurate snow densities varying as fast as 3 kHz. Because in a typical avalanche the scale of snow grains is on the order of 1 millimeter or less, with occasional clumps as large as a few centimeters, a good separation distance for the two sensor electrodes 204 and 206 should be approximately 15 mm. With the 3 kHz bandwidth of the amplifier output, a wide range of time lags can be recorded between the two sensor electrodes 204 and 206 which correspond to velocities less than or equal to 45 meters per second.

In summary, the present invention provides a number of guarded capacitance probe structures in which particular arrangements of guard electrodes are employed to confine the electric field lines generated by the probes in such a manner that very accurate measurements of fluid flow and particle concentration of fluid suspensions can be made. In particular, the relative dimensions of the guard electrodes are chosen so that all electric field lines emanating from the sensor electrode or electrodes will curve around and terminate on a nearby grounded surface with all of the field lines passing through a confined measurement volume of the fluid suspension. This arrangement, in which the relative positions of the sensor and ground electrodes are reversed, is advantageous because the resulting probe does not need to be calibrated and an electrical potential need not be applied to the vessel or pipe on which the probe is mounted.

Although the present invention has been disclosed in terms of a number of preferred embodiments, it will be understood that numerous variations and modifications could be made thereto without departing from the scope of the invention as set forth in the following claims.

What is claimed is:

1. A guarded capacitance probe structure comprising:

a sensor electrode having an aperture formed therein;

a guard electrode having an outer portion surrounding said sensor electrode and an inner portion contained within said aperture, said guard electrode being electrically insulated from said sensor electrode; and an electrically grounded surface surrounding said guard electrode and electrically insulated therefrom.

2. The probe structure of claim 1, further including;

means to apply a first electrical signal to said sensor electrode, wherein a voltage potential difference is formed between said sensor electrode and said grounded surface so that all electric field lines emanating from said sensor electrode curve over said surrounding portion of said guard electrode, and terminate on said grounded surface; and, means to apply a second electrical signal to said guard electrode, said second electrical signal having a voltage magnitude substantially equal to the voltage magnitude of said first electrical signal.

3. The probe structure of claim 1, wherein said sensor electrode is ring shaped and said aperture is centrally disposed in said sensor electrode.

4. The probe structure of claim 1, wherein said sensor and guard electrodes are attached to a surface of a vessel containing a fluid whose dielectric constant is to be measured by said probe structure, and said electrically grounded surface comprises an electrically conductive wall of said vessel.

5. The probe structure of claim 4, further including:

means to apply a first electrical signal to said sensor electrode, wherein a voltage potential difference is formed between said sensor electrode and said grounded surface so that all electric field lines emanating from said sensor electrode are confined to a small measurement volume of said fluid contained in said vessel, curve over said surrounding portion of said guard electrode and terminate on said electrically conductive wall of said vessel; and, means to apply a second electrical signal to said guard electrode, said second signal having a voltage magnitude substantially equal to the voltage magnitude of said first electrical signal.

6. The probe structure of claim 1, wherein said sensor and guard electrodes are formed integrally in a wall of a vessel containing a fluid whose dielectric constant is to be measured by said probe structure, and said electrically grounded surface is formed by said wall.

7. The probe structure of claim 6, further including:

means to apply a first electrical signal to said sensor electrode, wherein a voltage potential difference is formed between said sensor electrode and said grounded surface so that all electric field lines emanating from said sensor electrode are confined to a small measurement volume of said fluid contained in said vessel, curve over said surrounding portion of said guard electrode and terminate on said electrically conductive wall of said vessel; and, means to apply a second electrical signal to said guard electrode, said second signal having a voltage magnitude substantially equal to the voltage magnitude of said first electrical signal.

* * * * *